(12) United States Patent
Jennings et al.

(10) Patent No.: US 11,173,255 B2
(45) Date of Patent: Nov. 16, 2021

(54) INJECTION DEVICE

(71) Applicant: Cilag GmbH International, Zug (CH)

(72) Inventors: Douglas Ivan Jennings, Hertfordshire (GB); Ahmad Bitar, Cambridge (GB)

(73) Assignee: Cilag GmbH International, Zug (CH)

( * ) Notice: Subject to any disclaimer, the term of this patent is extended or adjusted under 35 U.S.C. 154(b) by 787 days.

(21) Appl. No.: 14/897,381

(22) PCT Filed: Jun. 11, 2014

(86) PCT No.: PCT/EP2014/062168
§ 371 (c)(1),
(2) Date: Dec. 10, 2015

(87) PCT Pub. No.: WO2014/198799
PCT Pub. Date: Dec. 18, 2014

(65) Prior Publication Data
US 2016/0129200 A1 May 12, 2016

Related U.S. Application Data

(63) Continuation of application No. PCT/EP2014/062168, filed on Jun. 20, 2014.

(30) Foreign Application Priority Data

Jun. 11, 2013 (GB) .................................... 1310392

(51) Int. Cl.
*A61M 5/32* (2006.01)
*A61M 5/20* (2006.01)

(52) U.S. Cl.
CPC ........ *A61M 5/3204* (2013.01); *A61M 5/2033* (2013.01); *A61M 2005/206* (2013.01); *A61M 2005/208* (2013.01)

(58) Field of Classification Search
CPC .............. A61M 5/3204; A61M 5/2033; A61M 5/31571; A61M 5/50; A61M 5/20;
(Continued)

(56) References Cited

U.S. PATENT DOCUMENTS 1,845,036 A 2/1932 Busher
2,019,382 A 10/1935 Aronson
(Continued)

FOREIGN PATENT DOCUMENTS

CA 2445511 A1 11/2002
CH 518102 A 1/1972
(Continued)

OTHER PUBLICATIONS

International Search Report dated Jul. 9, 2004; International Application No. PCT/GB03/05494.
(Continued)

*Primary Examiner* — Tiffany Legette
(74) *Attorney, Agent, or Firm* — Steven J. Schwarz

(57) ABSTRACT

An injection device comprises an actuator adapted when actuated to cause commencement of an injection sequence; a locking mechanism adapted to be moved between a locked position in which the locking mechanism prevents the actuator from being actuated, and an unlocked position in which the actuator can be actuated to cause commencement of the injection sequence. The locking mechanism comprises a contact portion which in the locked position of the locking mechanism projects against the actuator. The contact portion comprises a curved surface.

11 Claims, 4 Drawing Sheets

(58) Field of Classification Search
CPC ...... A61M 2005/206; A61M 2005/208; A61M 2005/2073; A61M 2005/2013
USPC .......................................................... 604/198
See application file for complete search history.

(56) References Cited

U.S. PATENT DOCUMENTS

| | | |
|---|---|---|
| 2,147,616 A | 2/1939 | Chaput |
| 2,295,849 A | 9/1942 | Kayden |
| 2,531,267 A | 11/1950 | Harisch |
| 2,752,918 A | 7/1956 | Rooseboom |
| 2,764,977 A | 10/1956 | Ferguson |
| 2,828,742 A | 4/1958 | Ashkenaz |
| 2,845,065 A | 7/1958 | Gabriel |
| 2,854,975 A | 10/1958 | Cohen |
| 3,076,455 A | 2/1963 | McConnaughey et al. |
| 3,131,692 A | 5/1964 | Love |
| 3,320,955 A | 5/1967 | Sarnoff |
| 3,329,146 A | 7/1967 | Waldman |
| 3,543,603 A | 12/1970 | Gley |
| 3,656,472 A | 4/1972 | Ben Moura |
| 3,674,033 A | 7/1972 | Powers |
| 3,702,608 A | 11/1972 | Tibbs |
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 3,976,069 A | 8/1976 | Ong |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,222,380 A | 9/1980 | Terayama |
| 4,231,368 A | 11/1980 | Becker |
| 4,236,516 A | 12/1980 | Nilson |
| 4,237,882 A | 12/1980 | Wickham |
| 4,299,238 A | 11/1981 | Baidwan et al. |
| 4,333,459 A | 6/1982 | Becker |
| 4,373,526 A | 2/1983 | Kling |
| 4,378,015 A | 3/1983 | Wardlaw |
| 4,394,863 A | 7/1983 | Bartner |
| 4,403,989 A | 9/1983 | Christensen et al. |
| 4,407,283 A | 10/1983 | Reynolds |
| 4,425,120 A | 1/1984 | Sampson et al. |
| 4,430,082 A | 2/1984 | Schwabacher |
| 4,500,310 A | 2/1985 | Christinger |
| 4,507,118 A | 3/1985 | Dent |
| 4,521,237 A | 6/1985 | Logothetis |
| 4,561,856 A | 12/1985 | Cochran et al. |
| 4,627,835 A | 12/1986 | Fenton, Jr. |
| 4,636,201 A | 1/1987 | Ambrose et al. |
| 4,639,250 A | 1/1987 | Rycroft |
| 4,642,099 A | 2/1987 | Phillips et al. |
| 4,676,530 A | 6/1987 | Nordgren et al. |
| 4,695,274 A | 9/1987 | Fox |
| 4,717,383 A | 1/1988 | Phillips et al. |
| 4,744,786 A | 5/1988 | Hooven et al. |
| 4,787,891 A | 11/1988 | Levin et al. |
| 4,874,383 A | 10/1989 | McNaughton |
| 4,874,384 A | 10/1989 | Nunez |
| 4,929,232 A | 5/1990 | Sweeney et al. |
| 4,969,870 A | 11/1990 | Kramer et al. |
| 4,988,339 A | 1/1991 | Vadher |
| 4,994,034 A | 2/1991 | Botich et al. |
| 5,009,646 A | 4/1991 | Sudo et al. |
| 5,026,349 A | 6/1991 | Schmitz et al. |
| 5,057,079 A | 10/1991 | Tiemann et al. |
| 5,073,170 A | 12/1991 | Schneider |
| 5,092,842 A | 3/1992 | Bechtold et al. |
| 5,098,400 A | 3/1992 | Crouse et al. |
| 5,112,119 A | 5/1992 | Cooke et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,147,325 A | 9/1992 | Mitchell et al. |
| 5,156,599 A | 10/1992 | Ranford et al. |
| 5,176,643 A | 1/1993 | Kramer et al. |
| 5,188,613 A | 2/1993 | Shaw |
| 5,190,526 A | 3/1993 | Murray et al. |
| 5,242,400 A | 9/1993 | Blake et al. |
| 5,242,416 A | 9/1993 | Hutson |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,312,364 A | 5/1994 | Jacobs |
| 5,330,081 A | 7/1994 | Davenport |
| 5,330,430 A | 7/1994 | Sullivan |
| 5,356,395 A | 10/1994 | Chen |
| 5,358,489 A | 10/1994 | Wyrick |
| 5,364,369 A | 11/1994 | Reynolds |
| 5,368,577 A | 11/1994 | Teoh et al. |
| 5,372,586 A | 12/1994 | Haber et al. |
| 5,385,551 A | 1/1995 | Shaw |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,503,627 A | 4/1996 | McKinnon et al. |
| 5,514,097 A | 5/1996 | Knauer |
| 5,520,653 A | 5/1996 | Reilly et al. |
| 5,540,660 A | 7/1996 | Jenson et al. |
| 5,540,666 A | 7/1996 | Barta et al. |
| 5,540,709 A | 7/1996 | Ramel et al. |
| 5,567,160 A | 10/1996 | Massino |
| 5,569,191 A | 10/1996 | Meyer |
| 5,569,192 A | 10/1996 | van der Wal |
| 5,575,777 A | 11/1996 | Cover et al. |
| 5,599,302 A | 2/1997 | Lilley et al. |
| 5,599,309 A | 2/1997 | Marshall et al. |
| 5,607,395 A | 3/1997 | Ragsdale et al. |
| 5,609,577 A | 3/1997 | Haber et al. |
| 5,609,584 A | 3/1997 | Gettig et al. |
| 5,611,785 A | 3/1997 | Mito et al. |
| 5,634,906 A | 6/1997 | Foster et al. |
| 5,637,094 A | 6/1997 | Stewart, Jr. et al. |
| 5,645,536 A | 7/1997 | Whisson |
| 5,647,845 A | 7/1997 | Haber et al. |
| 5,649,912 A | 7/1997 | Peterson |
| 5,658,259 A | 8/1997 | Pearson et al. |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,704,911 A | 1/1998 | Parsons et al. |
| 5,709,662 A | 1/1998 | Olive et al. |
| 5,713,866 A | 2/1998 | Wilmot |
| 5,748,316 A | 5/1998 | Wakabayashi et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,827,262 A | 10/1998 | Neftel et al. |
| 5,843,036 A | 12/1998 | Olive et al. |
| 5,855,839 A | 1/1999 | Brunel |
| 5,865,795 A | 2/1999 | Schiff et al. |
| 5,865,804 A | 2/1999 | Bachynsky |
| 5,868,711 A | 2/1999 | Kramer et al. |
| 5,879,327 A | 3/1999 | Moreau DeFarges et al. |
| 5,891,086 A | 4/1999 | Terrence et al. |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |

(56) References Cited

U.S. PATENT DOCUMENTS

| | | |
|---|---|---|
| 5,989,229 A | 11/1999 | Chiappetta |
| 5,997,513 A | 12/1999 | Smith et al. |
| 6,007,515 A | 12/1999 | Epstein et al. |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A | 7/2000 | Hager et al. |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross |
| 6,123,684 A | 9/2000 | Deboer et al. |
| 6,139,534 A | 10/2000 | Niedospial, Jr. et al. |
| 6,159,161 A | 12/2000 | Hodosh |
| 6,159,181 A | 12/2000 | Crossman et al. |
| 6,159,184 A | 12/2000 | Perez et al. |
| 6,162,199 A | 12/2000 | Geringer |
| 6,171,276 B1 | 1/2001 | Lippe et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 | 3/2001 | Stewart |
| 6,209,738 B1 | 4/2001 | Jansen et al. |
| 6,221,044 B1 | 4/2001 | Grecco |
| 6,228,055 B1 | 5/2001 | Foerster et al. |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,290,683 B1 | 9/2001 | Erez et al. |
| 6,293,925 B1 | 9/2001 | Safabash et al. |
| RE37,439 E | 11/2001 | Firth et al. |
| 6,317,939 B1 | 11/2001 | Malin |
| 6,330,960 B1 | 12/2001 | Faughey et al. |
| 6,332,875 B2 | 12/2001 | Inkpen et al. |
| 6,371,939 B2 | 4/2002 | Bergens et al. |
| 6,371,959 B1 | 4/2002 | Trice |
| 6,387,078 B1 | 5/2002 | Gillespie |
| 6,391,003 B1 | 5/2002 | Lesch |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 | 10/2002 | Frezza |
| 6,491,667 B1 | 12/2002 | Keane et al. |
| 6,517,517 B1 | 2/2003 | Farrugia et al. |
| 6,536,723 B1 | 3/2003 | Nakatani |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Aichas et al. |
| 6,569,124 B1 | 5/2003 | Perouse |
| 6,572,581 B1 | 6/2003 | Landua |
| 6,575,939 B1 | 6/2003 | Brunel |
| 6,579,269 B1 | 6/2003 | Kleyman |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,599,272 B1 | 7/2003 | Hjertman et al. |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landua |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau et al. |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,746,438 B1 | 6/2004 | Arnissolle |
| 6,767,336 B1 | 7/2004 | Kaplan |
| 6,770,056 B2 | 8/2004 | Price et al. |
| 6,776,777 B2 | 8/2004 | Barelle |
| 6,783,509 B1 | 8/2004 | Landau et al. |
| 6,793,161 B1 | 9/2004 | Fujia et al. |
| 6,796,967 B2 | 9/2004 | Jensen |
| 6,811,548 B2 | 11/2004 | Jeffrey |
| 6,817,987 B2 | 11/2004 | Vetter et al. |
| 6,846,303 B2 | 1/2005 | Eakins et al. |
| 6,875,205 B2 | 4/2005 | Leinsing |
| 6,890,319 B1 | 5/2005 | Crocker |
| 6,899,698 B2 | 5/2005 | Sams |
| 6,902,543 B1 | 6/2005 | Cherif-Cheikh et al. |
| 6,932,793 B1 | 8/2005 | Marshall et al. |
| 6,939,319 B1 | 9/2005 | Anstead et al. |
| 6,939,330 B1 | 9/2005 | McConnell et al. |
| 6,979,316 B1 | 12/2005 | Rubin et al. |
| 7,066,907 B2 | 6/2006 | Crossman et al. |
| 7,097,071 B2 | 8/2006 | Anderson et al. |
| 7,097,634 B2 | 8/2006 | Gilbert |
| 7,118,553 B2 | 10/2006 | Scherer |
| 7,156,823 B2 | 1/2007 | Landau et al. |
| 7,160,913 B2 | 1/2007 | Schneider |
| 7,294,122 B2 | 11/2007 | Kubo et al. |
| 7,354,427 B2 | 4/2008 | Fangrow |
| RE40,428 E | 7/2008 | Keane et al. |
| 7,442,185 B2 | 10/2008 | Amark et al. |
| 7,470,258 B2 | 12/2008 | Barker et al. |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,238 B2 | 5/2009 | Fangrow |
| 7,547,300 B2 | 6/2009 | Fangrow |
| 7,569,043 B2 | 8/2009 | Fangrow |
| 7,618,396 B2 | 11/2009 | Slate et al. |
| 7,635,356 B2 | 12/2009 | Stamp |
| 7,645,271 B2 | 1/2010 | Fangrow |
| 7,654,995 B2 | 2/2010 | Warren et al. |
| 7,658,733 B2 | 2/2010 | Fangrow |
| 7,678,333 B2 | 3/2010 | Reynolds et al. |
| 7,682,155 B2 | 3/2010 | Raven et al. |
| 7,682,345 B2 | 3/2010 | Savage |
| 7,717,879 B2 | 5/2010 | Mansouri |
| 7,744,561 B2 | 6/2010 | Stamp |
| 7,759,654 B2 | 7/2010 | Yan et al. |
| 7,785,292 B2 | 8/2010 | Harrison |
| 7,794,434 B2 | 9/2010 | Mounce et al. |
| 7,799,009 B2 | 9/2010 | Niedospial, Jr. et al. |
| 7,811,262 B2 | 10/2010 | Moberg et al. |
| 7,828,764 B2 | 11/2010 | Moberg et al. |
| 7,871,397 B2 | 1/2011 | Schraga |
| 7,879,010 B2 | 2/2011 | Hunn et al. |
| 7,883,499 B2 | 2/2011 | Fangrow |
| 7,959,715 B2 | 6/2011 | Kavazov et al. |
| 7,972,321 B2 | 7/2011 | Fangrow |
| 7,976,499 B2 | 7/2011 | Grunhut et al. |
| 8,100,154 B2 | 1/2012 | Reynolds et al. |
| 8,177,768 B2 | 5/2012 | Leinsing |
| 8,277,414 B2 | 10/2012 | Barrow-Williams et al. |
| 8,313,463 B2 | 11/2012 | Barrow-Williams et al. |
| 8,317,751 B2 | 11/2012 | Alheidt |
| 8,343,110 B2 | 1/2013 | Burnell |

(56) References Cited

U.S. PATENT DOCUMENTS

| | | |
|---|---|---|
| 8,409,138 B2 | 4/2013 | James et al. |
| 8,409,141 B2 | 4/2013 | Johansen et al. |
| 8,491,530 B2 | 7/2013 | Maritan |
| 8,556,861 B2 | 10/2013 | Tsais |
| 8,696,628 B2 | 4/2014 | Grunhut |
| 8,932,264 B2 | 1/2015 | DeSalvo |
| 8,968,236 B2 | 3/2015 | Jennings et al. |
| 9,028,451 B2 | 5/2015 | Jennings |
| 9,248,245 B2 | 2/2016 | Ekman et al. |
| 9,314,574 B2 | 4/2016 | Roberts et al. |
| 9,358,346 B2 | 6/2016 | Beyeler |
| 9,592,350 B2 | 3/2017 | Roberts et al. |
| 9,675,757 B2 | 6/2017 | Harrison |
| 9,757,520 B2 | 9/2017 | Corrigan |
| 10,588,983 B2 | 3/2020 | Bookbinder et al. |
| 2001/0005781 A1 | 6/2001 | Bergens et al. |
| 2001/0021826 A1 | 9/2001 | Fisher et al. |
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0039394 A1 | 11/2001 | Terrence et al. |
| 2001/0049496 A1 | 12/2001 | Kirchhofer et al. |
| 2001/0051789 A1 | 12/2001 | Parsons |
| 2002/0032412 A1 | 3/2002 | Riemelmoser |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078496 A1 | 4/2003 | Price |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sharpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0187405 A1 | 10/2003 | Gatti |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsais et al. |
| 2003/0233070 A1 | 12/2003 | De La Serna et al. |
| 2003/0236502 A1 | 12/2003 | De La Serna et al. |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0094396 A1 | 5/2004 | Lee et al. |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2004/0254526 A1 | 12/2004 | Terrence et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0113747 A1 | 5/2005 | Moir |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0165360 A1 | 7/2005 | Stamp |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0129089 A1 | 6/2006 | Stamp |
| 2006/0161111 A1 | 7/2006 | Potter et al. |
| 2006/0178630 A1 | 8/2006 | Bostrom et al. |
| 2006/0178631 A1 | 8/2006 | Gillespie et al. |
| 2006/0178642 A1 | 8/2006 | Gillespie et al. |
| 2006/0184119 A1 | 8/2006 | Remde et al. |
| 2006/0184137 A1 | 8/2006 | Reynolds |
| 2006/0189938 A1 | 8/2006 | Hommann et al. |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0021716 A1 | 1/2007 | Hansen |
| 2007/0027430 A1 | 2/2007 | Hommann |
| 2007/0032775 A1 | 2/2007 | Niedospial et al. |
| 2007/0066939 A1 | 3/2007 | Krulevitch et al. |
| 2007/0078382 A1 | 4/2007 | Hommann et al. |
| 2007/0078428 A1 | 4/2007 | Reynolds |
| 2007/0118094 A1 | 5/2007 | Bingham et al. |
| 2007/0135767 A1 | 6/2007 | Gillespie, II et al. |
| 2007/0142787 A1 | 6/2007 | Scherer |
| 2007/0150842 A1 | 6/2007 | Chaudhri et al. |
| 2007/0156091 A1 | 7/2007 | Fathallah et al. |
| 2007/0156112 A1 | 7/2007 | Walsh |
| 2007/0208296 A1 | 9/2007 | Paproski et al. |

(56) References Cited

U.S. PATENT DOCUMENTS

| | | |
|---|---|---|
| 2007/0244456 A1 | 10/2007 | Fangrow |
| 2007/0244457 A1 | 10/2007 | Fangrow |
| 2007/0244458 A1 | 10/2007 | Fangrow |
| 2007/0244459 A1 | 10/2007 | Fangrow |
| 2007/0244460 A1 | 10/2007 | Fangrow |
| 2007/0244461 A1 | 10/2007 | Fangrow |
| 2007/0244462 A1 | 10/2007 | Fangrow |
| 2007/0244463 A1 | 10/2007 | Warren et al. |
| 2007/0244464 A1 | 10/2007 | Fangrow et al. |
| 2007/0244465 A1 | 10/2007 | Fangrow |
| 2007/0244466 A1 | 10/2007 | Fangrow |
| 2008/0033395 A1 | 2/2008 | Alchas |
| 2008/0071225 A1 | 3/2008 | Hommann et al. |
| 2008/0154192 A1 | 6/2008 | Schraga |
| 2008/0161770 A1 | 7/2008 | Fangrow |
| 2008/0172001 A1 | 7/2008 | Reynolds et al. |
| 2008/0172024 A1 | 7/2008 | Yow |
| 2008/0213590 A1 | 9/2008 | Greiner et al. |
| 2008/0249462 A1 | 10/2008 | Nilufer et al. |
| 2008/0249498 A1 | 10/2008 | Fangrow |
| 2008/0262427 A1 | 10/2008 | Hommann |
| 2008/0269680 A1 | 10/2008 | Ibranyan et al. |
| 2008/0306443 A1 | 12/2008 | Neer et al. |
| 2008/0312592 A1 | 12/2008 | Barrow-Williams et al. |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Timothy Donald et al. |
| 2009/0149812 A1 | 6/2009 | MacAulay |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1 | 2/2010 | Drake et al. |
| 2010/0049125 A1 | 2/2010 | James et al. |
| 2010/0063444 A1 | 3/2010 | Wikner |
| 2010/0234811 A1 | 9/2010 | Schubert et al. |
| 2010/0286714 A1 | 11/2010 | Gyrn et al. |
| 2010/0292653 A1 | 11/2010 | Maritan |
| 2011/0092954 A1 | 4/2011 | Jennings |
| 2011/0098647 A1 | 4/2011 | Jennings |
| 2011/0098655 A1 | 4/2011 | Jennings et al. |
| 2011/0098656 A1 | 4/2011 | Burnell et al. |
| 2011/0130743 A1 | 6/2011 | Jennings et al. |
| 2011/0144594 A1* | 6/2011 | Sund ............ A61M 5/31571 604/228 |
| 2011/0172640 A1 | 7/2011 | Cronenberg et al. |
| 2011/0245761 A1 | 10/2011 | Dean et al. |
| 2011/0282278 A1 | 11/2011 | Stamp et al. |
| 2012/0046615 A1 | 2/2012 | Iwase et al. |
| 2012/0232491 A1 | 9/2012 | Jennings |
| 2012/0283698 A1 | 11/2012 | Millerd |
| 2012/0323177 A1 | 12/2012 | Adams et al. |
| 2013/0046246 A1 | 2/2013 | Boyd et al. |
| 2013/0060232 A1 | 3/2013 | Adlon et al. |
| 2013/0096512 A1 | 4/2013 | Ekman et al. |
| 2013/0125441 A1 | 5/2013 | Westwood et al. |
| 2013/0150801 A1 | 6/2013 | Barrow-Williams et al. |
| 2013/0267898 A1 | 10/2013 | Hourmand et al. |
| 2013/0310759 A1 | 11/2013 | Barrow-Williams et al. |
| 2013/0317446 A1 | 11/2013 | Hourmand et al. |
| 2013/0331794 A1 | 12/2013 | Ekman et al. |
| 2013/0338601 A1 | 12/2013 | Cowe |
| 2013/0345643 A1 | 12/2013 | Hourmand et al. |
| 2014/0207106 A1 | 7/2014 | Bechmann |
| 2014/0221974 A1 | 8/2014 | Bechmann et al. |
| 2014/0257185 A1 | 9/2014 | Bechmann et al. |
| 2014/0257193 A1 | 9/2014 | Bostrom et al. |
| 2015/0025458 A1 | 1/2015 | Heald et al. |
| 2015/0051551 A1 | 2/2015 | Hirschel et al. |
| 2015/0190590 A1 | 7/2015 | Macarthur et al. |
| 2018/0312590 A1 | 11/2018 | Cogswell et al. |

FOREIGN PATENT DOCUMENTS

| | | |
|---|---|---|
| CH | 703993 | 3/2012 |
| CN | 2059579 U | 7/1990 |
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 387465 | 1/1924 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 2/1997 |
| DE | 19603707 A1 | 8/1997 |
| DE | 69506521 T2 | 6/1999 |
| DE | 10137962 A1 | 2/2003 |
| DE | 10207276 A1 | 9/2003 |
| DE | 20311996 U1 | 11/2003 |
| EP | 0096314 A2 | 12/1983 |
| EP | 0144625 A2 | 6/1985 |
| EP | 0240787 A2 | 10/1987 |
| EP | 0338806 A2 | 10/1989 |
| EP | 0515473 B1 | 12/1992 |
| EP | 0518416 A1 | 12/1992 |
| EP | 0331452 B1 | 8/1993 |
| EP | 0389938 B1 | 5/1994 |
| EP | 0585626 A1 | 9/1994 |
| EP | 0516473 B1 | 2/1996 |
| EP | 0111724 B1 | 2/1998 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 1166809 B1 | 3/2004 |
| EP | 0666084 B1 | 4/2004 |
| EP | 0941133 B1 | 4/2004 |
| EP | 0991441 B1 | 12/2004 |
| EP | 1124601 B1 | 12/2004 |
| EP | 1364667 B1 | 4/2005 |
| EP | 1208858 B1 | 6/2006 |
| EP | 1586341 B1 | 1/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 1932558 B1 | 6/2011 |
| EP | 1755710 B1 | 3/2012 |
| EP | 2468330 A1 | 6/2012 |
| EP | 2340863 B1 | 11/2013 |
| EP | 2620174 B1 | 5/2014 |
| EP | 2675509 B1 | 4/2015 |
| EP | 2705861 B1 | 4/2015 |
| EP | 2319560 | 5/2015 |
| EP | 2414003 B1 | 5/2015 |
| EP | 2464401 B1 | 5/2015 |
| EP | 2493531 B1 | 7/2015 |
| EP | 2705862 B1 | 7/2015 |
| EP | 2268342 | 9/2015 |
| EP | 2588173 B1 | 10/2015 |
| EP | 2470241 B1 | 11/2015 |
| EP | 2768556 B1 | 12/2015 |
| EP | 2355872 B1 | 1/2016 |
| EP | 2720738 B1 | 1/2016 |
| EP | 1412000 B1 | 2/2016 |
| EP | 2671606 B1 | 3/2016 |
| EP | 2760507 B1 | 4/2016 |
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2654938 A1 | 5/1991 |

(56) References Cited

FOREIGN PATENT DOCUMENTS

| | | |
|---|---|---|
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 A | 5/1920 |
| GB | 412054 A | 6/1934 |
| GB | 728248 A | 4/1955 |
| GB | 909898 A | 11/1962 |
| GB | 1263355 A | 2/1972 |
| GB | 1311937 A | 3/1973 |
| GB | 1514725 A | 6/1978 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2443606 A * | 5/2008 .......... A61M 5/2033 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| GB | 2515041 B | 12/2014 |
| JP | 30-001091 | 1/1930 |
| JP | 49-77487 | 7/1974 |
| JP | 49-021036 | 6/1979 |
| JP | 54-087694 | 1/1982 |
| JP | 59-115053 A | 7/1984 |
| JP | 2-185261 A | 7/1990 |
| JP | 2-502971 T | 9/1990 |
| JP | 02-299660 A | 12/1990 |
| JP | 03-129156 | 12/1991 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | 07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-065786 | 3/2001 |
| JP | 2001-212237 A | 8/2001 |
| JP | 2002-500933 T | 1/2002 |
| JP | 2002-502296 A | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-154005 | 5/2003 |
| JP | 2003-284776 | 10/2003 |
| JP | 2003-532500 T | 11/2003 |
| JP | 2003-533288 A | 11/2003 |
| JP | 2004-033737 A | 2/2004 |
| JP | 2004-533282 T | 11/2004 |
| JP | 2004-537376 A | 12/2004 |
| JP | 2005-508214 A | 3/2005 |
| JP | 2005-177503 A | 7/2005 |
| JP | 2005-534433 | 11/2005 |
| JP | 2006-223858 A | 8/2006 |
| JP | 2007-207611 A | 8/2007 |
| JP | 2008-284177 A | 11/2008 |
| JP | 2008-295590 | 12/2008 |
| JP | 2008-543500 | 12/2008 |
| JP | 2012-503995 | 2/2012 |
| JP | 2013-529527 | 7/2013 |
| KR | 10-2008-0004473 | 1/2008 |
| NZ | 335985 A | 4/2001 |
| NZ | 573171 A | 11/2010 |
| NZ | 573350 A | 12/2010 |
| WO | 87/07843 A1 | 12/1987 |
| WO | 88/08725 A1 | 11/1988 |
| WO | 1988/10129 A1 | 12/1988 |
| WO | 92/19296 A | 11/1992 |
| WO | 93/21986 A2 | 11/1993 |
| WO | 1993/23098 A1 | 11/1993 |
| WO | 1993/02186 A1 | 12/1993 |
| WO | 1994/04207 A1 | 3/1994 |
| WO | 94/07554 A1 | 4/1994 |
| WO | 94/11041 A1 | 5/1994 |
| WO | 94/13342 A1 | 6/1994 |
| WO | 94/013343 | 6/1994 |
| WO | 94/21316 A1 | 9/1994 |
| WO | 94/22511 A1 | 10/1994 |
| WO | 95/04562 A1 | 2/1995 |
| WO | 95/31235 A1 | 11/1995 |
| WO | 1995/29720 A1 | 11/1995 |
| WO | 1995/35126 A1 | 11/1995 |
| WO | 95/35126 A1 | 12/1995 |
| WO | 96/30065 A1 | 10/1996 |
| WO | 97/10865 A1 | 3/1997 |
| WO | 1997/13538 A1 | 4/1997 |
| WO | 97/48430 A1 | 12/1997 |
| WO | 98/11927 A1 | 3/1998 |
| WO | 99/03529 A2 | 1/1999 |
| WO | 99/10030 A2 | 3/1999 |
| WO | 99/22789 A1 | 5/1999 |
| WO | 99/37343 A | 7/1999 |
| WO | 99/53979 A1 | 10/1999 |
| WO | 1999/59658 A1 | 11/1999 |
| WO | 00/06227 A1 | 2/2000 |
| WO | 00/07539 A1 | 2/2000 |
| WO | 00/13723 A2 | 3/2000 |
| WO | 00/24441 A1 | 5/2000 |
| WO | 00/35516 A1 | 6/2000 |
| WO | 00/50107 A1 | 8/2000 |
| WO | 00/61209 A1 | 10/2000 |
| WO | 00/64515 A1 | 11/2000 |
| WO | 00/69488 A2 | 11/2000 |
| WO | 01/05456 A1 | 1/2001 |
| WO | 01/49347 A1 | 7/2001 |
| WO | 01/60435 A1 | 8/2001 |
| WO | 01/76666 A1 | 10/2001 |
| WO | 01/077384 A2 | 10/2001 |
| WO | 01/87384 A1 | 11/2001 |
| WO | 02/11799 A1 | 2/2002 |
| WO | 02/47746 A1 | 6/2002 |
| WO | 02/056947 A1 | 7/2002 |
| WO | 02/074361 A2 | 9/2002 |
| WO | 03/013632 A2 | 2/2003 |
| WO | 03/015846 A2 | 2/2003 |
| WO | 03/015853 A1 | 2/2003 |
| WO | 03/039633 A2 | 5/2003 |
| WO | 03/041768 A | 5/2003 |
| WO | 03/047663 A2 | 6/2003 |

(56) References Cited

FOREIGN PATENT DOCUMENTS

| | | |
|---|---|---|
| WO | 03/051434 A2 | 6/2003 |
| WO | 03/066141 A1 | 8/2003 |
| WO | 03/092771 A1 | 11/2003 |
| WO | 03/097133 A1 | 11/2003 |
| WO | 03/099358 A2 | 12/2003 |
| WO | 04/007554 A1 | 1/2004 |
| WO | 04/011065 A1 | 2/2004 |
| WO | 2004/030732 A2 | 4/2004 |
| WO | 2004/035117 A2 | 4/2004 |
| WO | 2004/047890 A1 | 6/2004 |
| WO | 2004/047891 A1 | 6/2004 |
| WO | 2004/047892 A | 6/2004 |
| WO | 2004/054644 A1 | 7/2004 |
| WO | 2004/054645 A3 | 7/2004 |
| WO | 2004/087242 | 10/2004 |
| WO | 2004/087242 A1 | 10/2004 |
| WO | 2004/101025 A2 | 11/2004 |
| WO | 2004/108194 A1 | 12/2004 |
| WO | 2005/004961 A1 | 1/2005 |
| WO | 2005/009515 A1 | 2/2005 |
| WO | 2005/023341 A1 | 3/2005 |
| WO | 2005/025636 A2 | 3/2005 |
| WO | 2005/030301 A1 | 4/2005 |
| WO | 2005/035028 A1 | 4/2005 |
| WO | 2005/044345 A | 5/2005 |
| WO | 2005/044347 A1 | 5/2005 |
| WO | 2005/044348 | 5/2005 |
| WO | 2005/056077 | 6/2005 |
| WO | 2005/058393 A2 | 6/2005 |
| WO | 2005/058396 A1 | 6/2005 |
| WO | 2005/070481 A1 | 8/2005 |
| WO | 2005/082438 A1 | 9/2005 |
| WO | 2005/097238 A3 | 10/2005 |
| WO | 2005/105014 A2 | 11/2005 |
| WO | 2005/115507 A1 | 12/2005 |
| WO | 2005/115508 A1 | 12/2005 |
| WO | 2005/115509 A1 | 12/2005 |
| WO | 2005/115510 A1 | 12/2005 |
| WO | 2005/115512 A1 | 12/2005 |
| WO | 2005/115513 A1 | 12/2005 |
| WO | 2005/115514 A1 | 12/2005 |
| WO | 2005/115516 A1 | 12/2005 |
| WO | 2005/120607 A2 | 12/2005 |
| WO | 2006/008086 A1 | 1/2006 |
| WO | 2006/044236 A2 | 4/2006 |
| WO | 2006/050304 A1 | 5/2006 |
| WO | 2006/062788 A2 | 6/2006 |
| WO | 2006/063015 A2 | 6/2006 |
| WO | 2006/063124 A2 | 6/2006 |
| WO | 2006/088513 A1 | 8/2006 |
| WO | 2006/088630 A2 | 8/2006 |
| WO | 2006/099441 A2 | 9/2006 |
| WO | 2006/106290 A1 | 10/2006 |
| WO | 2006/106291 A1 | 10/2006 |
| WO | 2006/106292 A1 | 10/2006 |
| WO | 2006/106293 A1 | 10/2006 |
| WO | 2006/106294 A | 10/2006 |
| WO | 2006/106295 A1 | 10/2006 |
| WO | 2006/118616 A1 | 11/2006 |
| WO | 2006/129196 A1 | 12/2006 |
| WO | 2007/027204 A2 | 3/2007 |
| WO | 2007/036676 A1 | 4/2007 |
| WO | 2007/047200 A1 | 4/2007 |
| WO | 2007/051330 A1 | 5/2007 |
| WO | 2007/066152 A | 6/2007 |
| WO | 2007/066152 A2 | 6/2007 |
| WO | 2007/083115 | 7/2007 |
| WO | 2007/122193 A1 | 11/2007 |
| WO | 2007/129324 A2 | 11/2007 |
| WO | 2007/131013 A | 11/2007 |
| WO | 2007/138299 A1 | 12/2007 |
| WO | 2008/047372 A2 | 4/2008 |
| WO | 2008/059233 A1 | 5/2008 |
| WO | WO-2008059233 A1 * | 5/2008 ......... A61M 5/2033 |
| WO | 2008/075033 A | 6/2008 |
| WO | 2008/093063 A2 | 8/2008 |
| WO | 2010/023303 A1 | 3/2010 |
| WO | 2010/056712 | 5/2010 |
| WO | 2011/117283 | 9/2011 |
| WO | 2012/000835 A1 | 1/2012 |
| WO | 2012/059517 | 5/2012 |
| WO | 2012/093071 | 7/2012 |
| WO | 2012/117252 | 9/2012 |
| WO | 2012/140088 | 10/2012 |
| WO | 2012/155035 | 11/2012 |
| WO | 2013/070715 | 5/2013 |

OTHER PUBLICATIONS

International Search Report dated Sep. 5, 2005; International Application No. PCT/GB2005/002117.
International Search Report dated May 30, 2006; International Application No. PCT/GB2005/003725.
International Search Report dated Sep. 9, 2005; International Application No. PCT/GB2005/002126.
International Search Report dated Sep. 5,2005; International Application No. PCT/GB2005/002131.
International Search Report dated Sep. 9, 2005; International Application No. PCT/GB2005/002120.
International Search Report dated Sep. 5, 2005; International Application No. PCT/GB2005/002137.
International Search Report dated Sep. 6, 2005; International Application No. PCT/GB2005/002108.
International Search Report dated Sep. 5, 2005; International Application No. PCT/GB2005/002105.
International Search Report dated Sep. 5, 2005; International Application No. PCT/GB2005/002116.
International Search Report dated Sep. 5, 2005; International Application No. PCT/GB2005/002128.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Oct. 9, 2007; International Application No. PCT/GB2006/001023.
International Search Report dated Feb. 27, 2007; International Application No. PCT/IB2006/002792.
International Search Report dated Aug. 22, 2007; International Application No. PCT/GB2007/001992.
International Search Report dated Sep. 4, 2007; International Application No. PCT/GB2007/002002.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
International Search Report dated Oct. 14, 2008; International Application No. PCT/GB2008/002580.
International Search Report dated Nov. 27, 2008; International Application No. PCT/GB2008/002579.
International Search Report dated Oct. 10, 2008; International Application No. PCT/GB2008/002573.
International Search Report dated Oct. 10, 2008; International Application No. PCT/GB2008/002583.

(56) References Cited

OTHER PUBLICATIONS

International Search Report dated Sep. 30, 2009; International Application No. PCT/GB2009/001447.
International Search Report dated Oct. 2, 2009; International Application No. PCT/GB2009/001448.
International Search Report dated Oct. 5, 2009; International Application No. PCT/GB2009/001451.
International Search Report dated Oct. 6, 2009; International Application No. PCT/GB2009/001453.
International Search Report dated Oct. 5, 2009; International Application No. PCT/GB2009/001445.
International Search Report dated Jan. 22, 2010; International Application No. PCT/GB2009/001446.
International Search Report dated Jan. 12, 2008; International Application No. PCT/GB2008/002475.
International Search Report dated Sep. 4, 2003; International Application No. PCT/GB03/01946.
International Search Report dated Sep. 8, 2014; International Application No. PCT/EP2014/062163.
International Search Report dated Sep. 8, 2014; International Application No. PCT/EP2014/062166.
International Search Report dated Sep. 17, 2014; International Application No. PCT/EP2014/062167.
International Search Report dated Jan. 29, 2015; International Application No. PCT/EP2014/062167.
International Search Report dated Sep. 9, 2014; International Application No. PCT/EP2014/062168.
International Search Report dated Sep. 8, 2014; International Application No. PCT/EP2014/062162.
International Search Report dated Sep. 16, 2014; International Application No. PCT/EP2014/062160.
Page entitled 'Unusual cams' V. Ryan, 2002-2009; from www.technologystudent.com.
Cam Design and Manufacture; Preben W. Jensen; Industrial Press; New York; 1965; Chapter 1.
Definition of a cam taken from www.Wikipedia.com, Feb. 7, 2012.
Farm gate latch image Website showing gate latches from Mar. 6, 2004, http://dictionary.cambridge.org/dictionary/british/latch.
Engineering Tolerance, definition, Aug. 15, 2013; http://en.wikipedia.org/wiki/Engineering_tolerance.
Witness statement by Mr. Jeremy Marshal, Head of Technology Development & CI of the opponent, Dec. 2, 2011.
Patient instruction leaflet Glaxo Mode d'emploi (FR); Referred to in Statement of Jeremy Marshall, Dec. 2, 2011.
Assembly instructions, process flow diagrams for AJ1200CE129 and AJ1200CA00 together with drawings for AJ501 all dated differently; starting in 1993 and the latest dates referring to 2002, Referred to in Statement of Jeremy Marshall, Dec. 2, 2011.
Discussion session at the 5th International Nurses' Workshop on Multiple Sclerosis Nov. 30, 2011
Article from diabetes health, Jan. 2, 1997.
Parts list AJ503 Auto injector—Glaxo Jul. 19, 1992 (change 92-7-45)/Oct. 18, 1993 with drawings dated between 1986 and 1991.
Photos of a sample, Referred to in Statement of Jeremy Marshall, Dec. 2, 2011.
Company's sales ledger for the period of Nov. 1991-May 1993.
510(k) pre-market notification Apr. 19, 1990.
Fax dated Jul. 21, 1995 Imigran injection launch data.
Patient instruction leaflet, Imigran, Referred to in Statement of Jeremy Marshall, Dec. 2, 2011.
Patient instruction leaflet Glaxo Neurologie (NL), Referred to in Statement of Jeremy Marshall, Dec. 2, 2011.
Parts list AJ501 stamped Jun. 8, 2002.
Patient instruction leaflet Imigran (EN), Referred to in Statement of Jeremy Marshall, Dec. 2, 2011.
Detailed view of the retainer component AJ613 dated Jun. 15, 1993 last amended Nov. 8, 1995.
Production drawing Nov. 18, 2003, Autoject2 fixed needle AJ-0530-00-00-33.
Bill of material amendments log, Dec. 2, 2011.
Internet archive pages dated Dec. 4, 1999_1.
Internet archive pages dated Dec. 4, 1999_2
Invoices of sales Dec. 12, 2005 Autoject 2—Product code AJ1300EA000 and invoice of sales Mar. 21, 2006 Autoject 2—Product code AJ1311EA000.
Hospital price list Mar. 1990 and pharmacy trade price list Mar. 1994 losing an Autoinjector AJ1200.
Production record of Feb. 15, 2001 referring to device part AJ501 and a packaged part No. AJ1200CA00, Feb. 15, 2001
Production record, dated raised Feb. 15, 2001.
Parts list for AJ501, Referred to in Statement of Jeremy Marshall, Dec. 2, 2011.
General assembly drawing issued MAy 5, 1986, last amended Feb. 9, 1994.
Extracts from the company's sales ledger, Referred to in Statement of Jeremy Marshall, Dec. 2, 2011.
Extract from a medical shop catalogue, Referred to in Statement of Jeremy Marshall, Dec. 2, 2011.
Mechanical Engineer's Handbook; Dan B. Marghitu, J. David Irwin; Academic Press, Burlington, 2001.
Non-patent literature ISO 11040-4:1996('E').
European Pharmacopeia, 2002, p. 282-283.
"Starlock Fasteners": filed at the EPO by way of the opponent's letter of Apr. 3, 2013 and said to be retrieved from the website www.bakfin.com around that time.
Worksheet referred to in document A21; V. Ryan, 2002-2009; from www.technologystudent.com.
Dictionary definition of a latch; http://dictionary.cambridge.ora/dictionary/bristish/latch, Oct. 12, 2014.
"Farm Gate Latch Image": filed at the EPO by way of the opponent's letter of Oct. 31, 2014.
GA drawing dated Jun. 10, 1994 several times amended.
Article Apr. 27, 2002 5th International Nurses' Workshop on Multiple Sclerosis.

* cited by examiner

INJECTION DEVICE

FIELD OF THE INVENTION

The present invention relates to an injection device of the type that receives a syringe, extends it, discharges its contents and then retracts it automatically.

BACKGROUND OF THE INVENTION

Previously known injection devices are shown in WO 95/35126 and EP-A-0 516 473 and tend to employ a drive spring and a trigger that, when activated, causes the drive spring to act on the syringe when a releasable locking mechanism is also engaged.

An auto-injector is known from WO 2007/036676 which has a locking mechanism which must be disengaged before the release mechanism can be activated. In its locked position, the locking mechanism also prevents forward movement of the syringe out of the injection device against the bias of the return spring, for example when a cap gripping a boot covering the syringe needle, is removed. In the injection device described in WO 2007/036676, the locking mechanism comprises a sleeve which protrudes from an open end of the injection device. The sleeve is biased into its extended position by a resilient spring mechanism which must be overcome to disengage the locking mechanism. The locking mechanism can be disengaged by, for example, moving the sliding sleeve inwardly into the injection device (i.e. retracting the sleeve). This can be done by forcing the end of the sliding sleeve against tissue and then activating the release mechanism.

Generally, the trigger is rotatable about an axis so that when it is depressed at a first end, a second end (which normally engages the drive spring) is also rotated, thereby releasing the drive spring, extending the syringe and discharging its contents. The trigger comprises a protrusion which is engageable with a cut-out on the releasable locking mechanism when the releasable locking mechanism is engaged, thereby allowing the trigger to be activated. When the releasable locking mechanism is not engaged, the protrusion abuts a portion of the releasable locking mechanism preventing rotation of the trigger and release of the drive spring. This way, accidental activation of the trigger can be prevented.

A problem with an injection device of this type is that the protrusion on the trigger flexes when a force is applied to the trigger and the releasable locking mechanism is not engaged. A strong force applied to the trigger can cause enough flex in the protrusion that the end of the protrusion can engage the cut-out on the releasable locking mechanism, thereby allowing the trigger to be activated even when the releasable locking mechanism has not been engaged.

WO2006/106293 discloses an injection device which addresses this problem. In that case, the trigger includes a first portion having a cut-out therein, the first portion extending from a first end of the trigger in a direction substantially parallel to the first axis. The releasable locking mechanism includes a protrusion along a second axis for communicating with the first portion of the trigger when the releasable locking mechanism is in its first position and for communicating with the cut-out when the releasable locking mechanism is in its second position.

It was found that when a force is applied to the trigger when the locking mechanism is in its first position (i.e. engaged), the first portion of the trigger and the protrusion both flex in such a way that the protrusion is forced away from the cut-out, thereby decreasing the risk of accidental activation of the trigger still further.

However, it has been found that users of injection devices, such as those described in WO2007/036676 and WO 2006/106293, struggle to operate the device correctly. In particular, users struggle to actuate the trigger when the sliding sleeve has been retracted, either because the sliding sleeve has not quite been retracted sufficiently, or because the overall force required to actuate the trigger is too great. Because tolerances for these components is often very tight, there is often a very small, or no, margin of error in the distance to which the sliding sleeve must be retracted before triggering is possible. This can be very frustrating for users, since they may make numerous unsuccessful attempts at activating the injection since they are unaware that the sliding sleeve has not been fully retracted. Further, the frustrated user may attempt to force the injection device, i.e. by applying excessive pressure to the trigger, and so damage the injection mechanism.

One solution to the aforementioned problem is to ensure that the user knows whether or not the sliding sleeve is fully retracted, such that he or she does not attempt to actuate the trigger too early. Such solutions are helpful, but often the effort required to fully retract the sliding sleeve is too great, or else it is sufficient for the sleeve to have been retracted to within a particular tolerance.

There is therefore a need to provide an injection device that facilitates triggering of the device. The present invention addresses such a problem.

SUMMARY OF THE INVENTION

The injection device of the present invention is designed to deal with this and other problems. In a first aspect, the present invention provides an injection device comprising an actuator adapted when actuated to cause commencement of an injection sequence. The injection device further comprises a locking mechanism adapted to be moved between a locked position in which the locking mechanism prevents the actuator from being actuated, and an unlocked position in which the actuator can be actuated to cause commencement of the injection sequence. The locking mechanism comprises a contact portion which in the locked position of the locking mechanism projects against the actuator. The contact portion comprises a curved surface.

In the present specification, the term 'curved' means any rounded surface which results in the contact between the contact portion and the actuator to be a substantially 1-dimensional line or a point, rather than a 2-dimensional surface. It is often easier to determine that the contact portion is out of contact with the actuator if the contact between the portion and the actuator is a 1-dimensional line or a point, rather than a 2-dimensional surface. This also facilitates the manufacturing process, since tolerances need not be so accurate.

The provision of a curved surface on a contact portion reduces the overall force necessary to actuate the actuator (e.g. trigger) when the locking mechanism (e.g. sliding sleeve) has been retracted, or nearly retracted, without materially affecting the safety of the device. It is also possible to retract the locking mechanism whilst a force is exerted on the actuator, which is often convenient for users with reduced dexterity.

Moreover, the curved surface of the contact portion may assist in retracting the locking mechanism. The curved surface may, for example, be arranged with respect to the actuator such that once the locking mechanism has been retracted sufficiently (by engagement with a user's skin, for example), the act of exerting a force on the actuator will result in the actuator retracting the locking mechanism still further, as described further below.

In certain embodiments, the locking mechanism is adapted such that the contact potion is not in contact with the engagement surface of the actuator when the locking mechanism is in its locked position. In other words, in certain embodiments, the contact portion is adapted to contact an engagement surface of the actuator when the locking mechanism is in its locked position. The engagement surface may be a planar surface, and may be perpendicular with respect to the longitudinal axis of the injection device, or inclined with respect to that axis. The angle of inclination may be tailored as desired to achieve the necessary force required to activate the device. For example, the surface may be inclined toward a cut-out portion (mentioned above) so as to increase likelihood of successful engagement, or may be away from the cut-out portion so as to decrease the likelihood of accidental engagement.

The locking mechanism may be adapted such that the curved surface of the contact portion is in contact with the engagement surface over only a sub part of the contact portion when the locking mechanism is not in its unlocked position. In other words, when the locking mechanism is not in its unlocked position, the curved surface of the contact portion may be adapted to contact the engagement surface over only a sub-part of the contact portion. The size of the sub-part may be adjusted depending on the force required to activate the device.

The locking mechanism may be adapted such that the contact position is not in contact with the engagement surface of the actuator when the locking mechanism is in its unlocked position. In other words, the contact portion may be adapted not to contact an engagement surface of the actuator when the locking mechanism is in its unlocked position. In other words, when the locking mechanism is fully retracted, the contact surface may be entirely clear of the engagement surface.

The locking mechanism is preferably moveable between its locked position and its unlocked position such that the contact portion moves from a position in which it contacts the engagement surface of the actuator to a position in which it no longer contacts the engagement surface of the actuator.

In preferred arrangements, the locking mechanism slides between its locked position and unlocked position along a first axis A. For example, the locking mechanism may be a sliding sleeve which is slidable upon engagement with a user's skin. The first axis A may be parallel with the longitudinal axis of the injection device.

The contact portion may comprise a first projection which extends from the locking mechanism. Preferably, the first projection extends along a second axis B.

The engagement surface may be a surface on a first portion which extends from the actuator. Preferably, the first projection extends along third axis C.

In particularly preferred embodiments, the second axis B and third axis C intersect each other with an intersection angle of between 45 and 90 degrees, 60 and 90 degrees, 80 and 90 degrees, or 90 degrees. Moreover, in a further preferred embodiment, the first axis A and third axis C are parallel to each other. In a further preferred embodiment the second axis B intersects both the first axis A and the third axis C. The relationships between the axes described above may be provided independently of each other.

The actuator may be configured to move between a first position, in which commencement of the injection sequence is prevented, and a second position in which commencement of the injection sequence occurs. For example, the injection device may further comprise a drive mechanism, wherein the actuator comprises a locking surface which inhibits the drive mechanism when the actuator is in its first position and which does not inhibit the drive mechanism when the drive mechanism is in its second position. A direct relationship between the actuator and a drive mechanism is a convenient and reliable implementation.

Preferably the actuator rotates between its first and second positions about a pivot. This facilitates actuation of the actuator, particularly for those with reduced dexterity. Where a pivot is provided, it is particularly preferred if the axis of the pivot and the second axis B substantially intersect each other with an intersection angle of between 45 and 90 degrees, 60 and 90 degrees, 80 and 90 degrees, or 90 degrees.

Preferably the injection device further comprises a syringe which is moveable by the drive mechanism on commencement of the injection sequence from a position in which the syringe is wholly contained within a body of the injection device to a position in which a needle of the syringe extends from the body of the injection device via an opening. The drive mechanism may be adapted to expel contents of the syringe via the needle when the syringe is in its extended position.

In any embodiment, the injection device may contain a substance selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

By 'the injection device may contain a substance' it is meant that the substance may be contained within a suitable medicament container, such as a vial or syringe, within the injection device. Such medicament container may contain other substances, such as further active or inactive ingredients.

In a further aspect of the invention, a substance is provided, the substance being selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity, by delivery of said substance to a human subject using an injection device according to any of the above embodiments.

In yet another aspect of the invention, an injection device is provided for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity, by delivery of a substance selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, to a human subject by using the injection device, where the injection device is an injection device of any of the above embodiments.

By 'delivery of a substance' it is meant that the injection device is used to inject said substance into the human subject, for example by subcutaneous, intradermal or intramuscular injection. Said substance may be administered in combination with other substances, such as further active or inactive ingredients.

BRIEF DESCRIPTION OF THE DRAWINGS

The invention will now be described by way of example with reference to the accompanying drawings, in which.

DETAILED DESCRIPTION OF THE DRAWINGS

FIGS. 1 to 4 show an exemplary injection device 110. The injection device 110 has an injection device housing 112 and a longitudinal axis 101.

Figure 1:
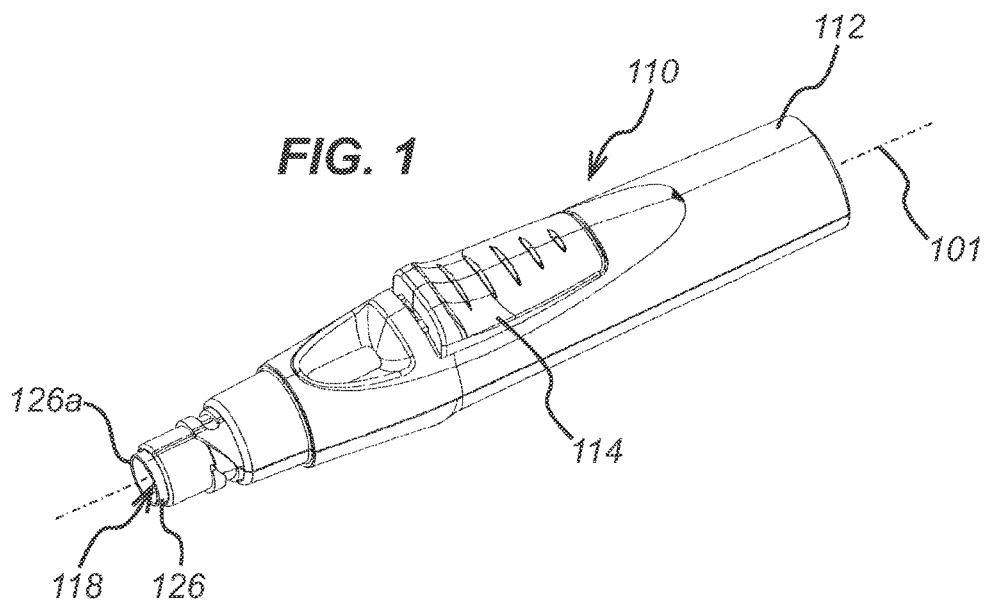
FIG. 1 shows a perspective view of an exemplary injection device.
Figure 2:
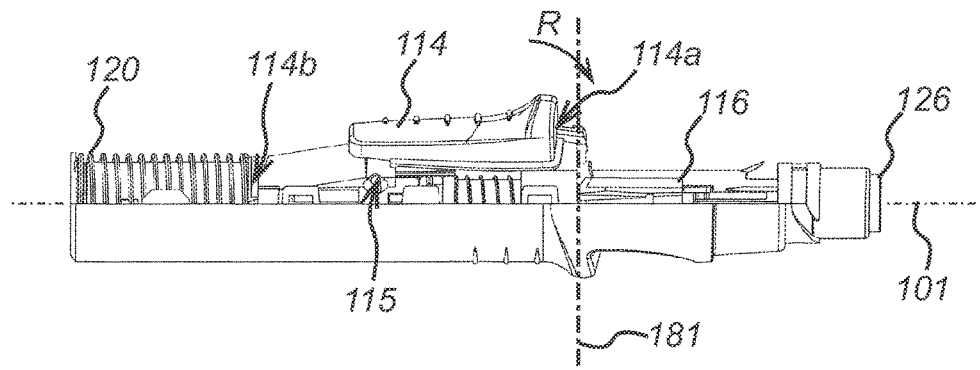
FIG. 2 shows a side view of the injection device of FIG. 1 with an upper section of its housing not shown.
Figure 3:
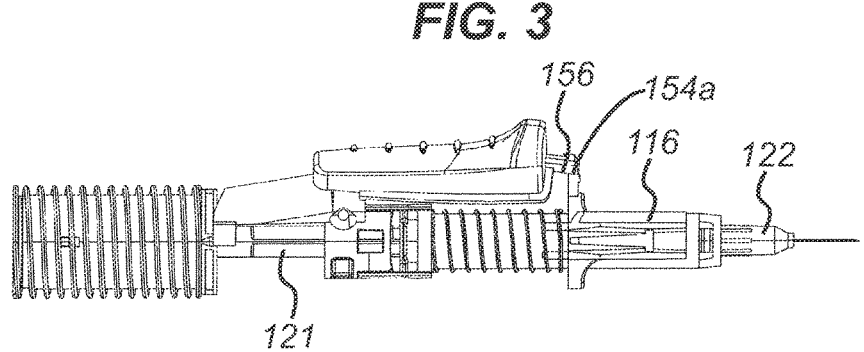
FIG. 3 shows a side view of the injection device of FIG. 2 with further components not shown.

A syringe 122 is contained in the housing 112. The injection device 110 comprises trigger 114 and a releasable locking mechanism 116. The trigger 114 has a first end 114a and a second end 114b. The trigger 114 is rotatable about a pivot 115 from a rest position (as shown in FIG. 2) to an active position. The second end 114b of the trigger 114 connects with a drive coupling 121 which is acted upon by a drive spring 120. The drive coupling 121 is in communication with the syringe 122.

Rotation of the trigger 114 about the pivot 115 in a direction R (i.e. downwards into the housing 112 at its first end 114a) causes the second end 114b of the trigger 114 to disengage from the drive coupling 121, thereby letting the drive spring 120 drive the syringe 122 (via the drive coupling 121) along the longitudinal axis 101 and out of an aperture 118 in the housing 112.

The releasable locking mechanism 116 is in communication with sliding sleeve 126 which protrudes, when in a first position, from the aperture 118 in the housing 112. The locking mechanism 116 is deactivated by movement of the sliding sleeve 126 along the longitudinal axis 101 into the housing 112 into a second position.

A first end 126a of the sliding sleeve 126 can be placed against a body into which drug is being delivered, thereby deactivating the releasable locking mechanism 116 and allowing the trigger 114 to rotate in direction R from its rest position to its active position.

Figure 5:
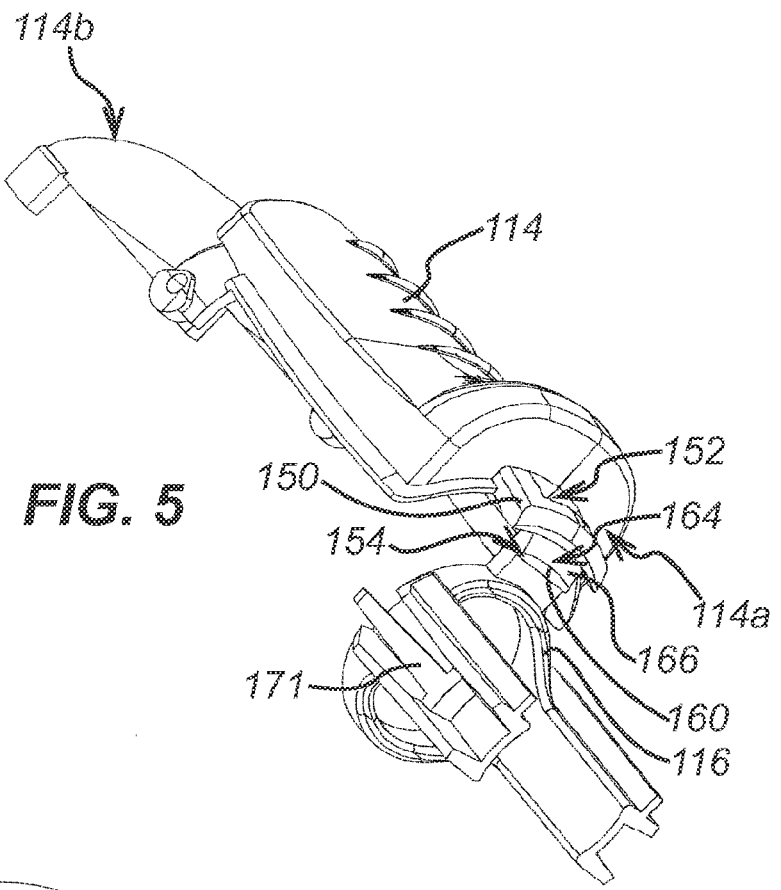
FIG. 5 shows a perspective view of an exemplary trigger and releasable locking mechanism.
Figure 6:
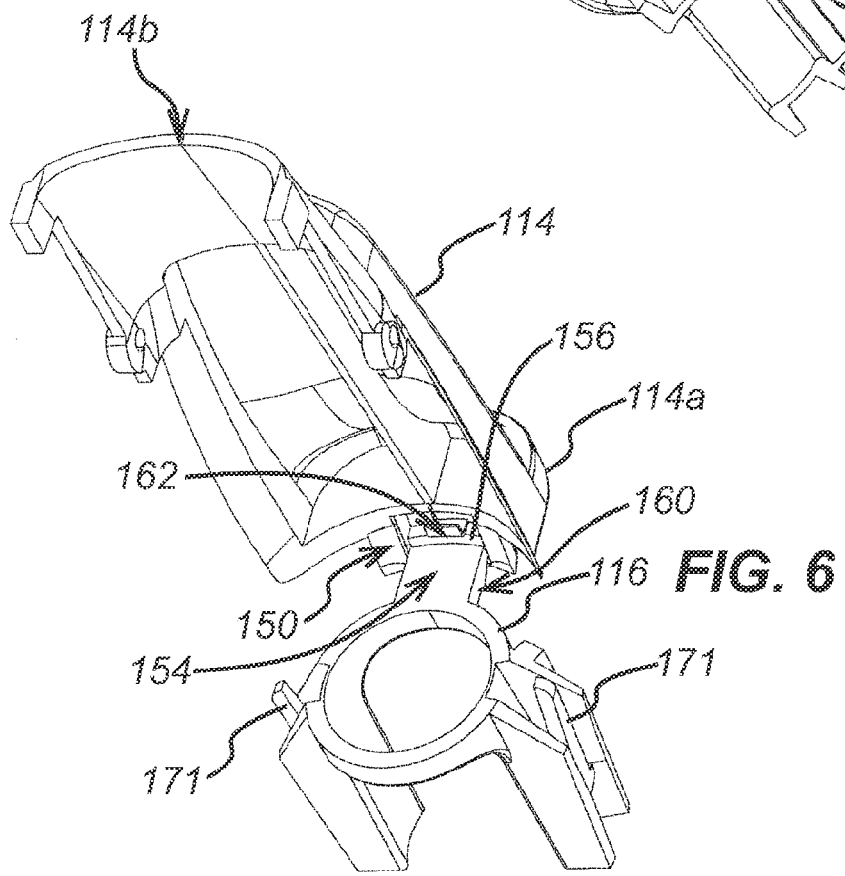
FIG. 6 shows an alternative perspective view of the trigger and releasable locking mechanism of FIG. 5.

As can be seen from FIGS. 5 and 6, the trigger 114 is provided at its first end 114a with a first portion 150 having a cut-out 152. The first portion 150 extends from the first end 114a of the trigger 114a in a direction substantially parallel to the longitudinal axis 101.

The releasable locking mechanism 116 includes a protrusion 154 which projects in a direction along a perpendicular axis 181 which is perpendicular to the longitudinal axis 101. The cut-out 152 is dimensioned to receive the protrusion 154.

When the releasable locking mechanism 116 is in its first position, an end 154a of the protrusion 154 abuts an undersurface 156 of the first portion 150, thereby preventing rotation of the trigger 114.

When the releasable locking mechanism 116 is in its second position (not shown) following movement of the sliding sleeve 126 into the housing 112, the cut-out 152 is positioned above the end of the protrusion 154 allowing it to pass over the protrusion 154 when a downwards force is applied the trigger 112. Hence, the trigger 112 is no longer prevented from rotating and disengages itself from the drive coupling 121, thereby extending the syringe 122.

The protrusion 154 comprises a first ridge 160. The trigger 114 includes a second portion 162 which extends into the cut-out 152 from the first portion 150 of the trigger 114 and which is arranged to communicate with the second portion 162 following rotation of the trigger 114 so that the first ridge 160 is locked over the second portion 162, thereby preventing movement of the trigger 114 from its active position back to its rest position.

The locking mechanism 116 includes biasing means, in the form of resilient arms 171, which act against the internal surface of the housing 112 to bias the locking mechanism 116 and sliding sleeve 126 in a direction out of aperture 118. This way, following activation of the trigger 112, the first ridge 160 is locked over the second portion 162 of the trigger 112, thereby holding the trigger 112 in its active position.

The first portion 150 of the trigger comprises a second ridge 164 on the under-surface 156 of the first portion 150 which is positioned between the cut-out 152 and the end of the first portion 150. The second ridge 164 abuts the protrusion 154 when force is applied to the trigger 114 in a direction R and the release mechanism is in its first (i.e. engaged) position. This prevents the protrusion 154 from moving into a position in which its end 154a moves over the end of the first portion 150 which would allow the trigger 114 to rotate whilst the releasable locking mechanism 116 was still engaged, thereby accidentally "firing" the injection device 110.

The protrusion 154 has a sloped surface 166 which is angled with respect to the second axis 181 which allows the second portion 162 of the trigger 114 to pass over the protrusion 154 more effectively when the trigger 114 is rotated and the releasable locking mechanism 116 is disengaged.

The first portion 150 is angled away from the cut-out 152 such that cut-out is deflected away from the cut-out when a force is applied to the trigger 114 and the locking mechanism is disengaged.

Figure 4:
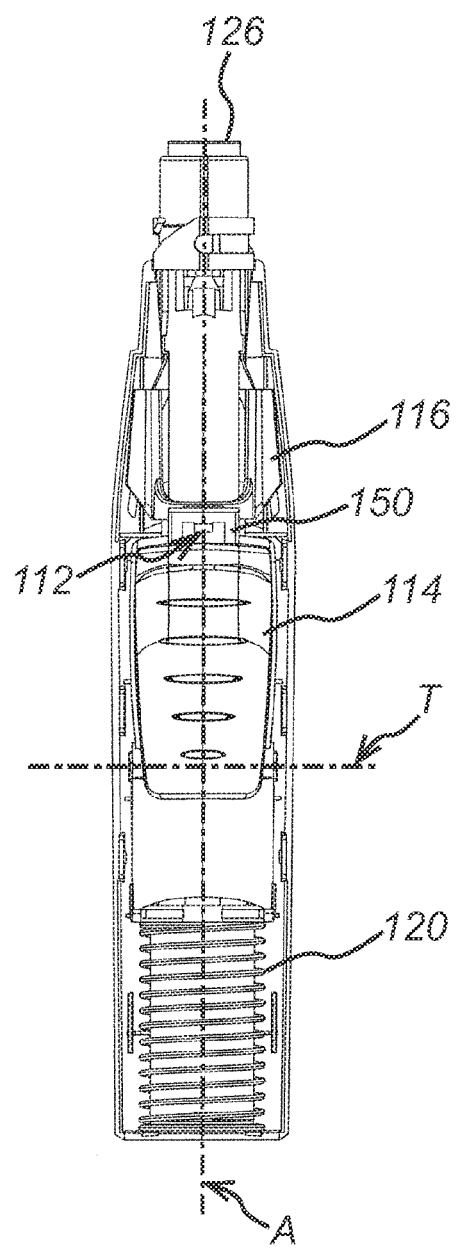
FIG. 4 shows a top plan view of the injection device of FIG. 2.

FIG. 4 shows two axes. Axis 'A' is parallel to the longitudinal axis of the injection device and along which the sliding sleeve 126 slides in the manner described above. Axis 'T' is a trigger axis which is the axis about which trigger 114 is configured to rotate.

Figure 7:
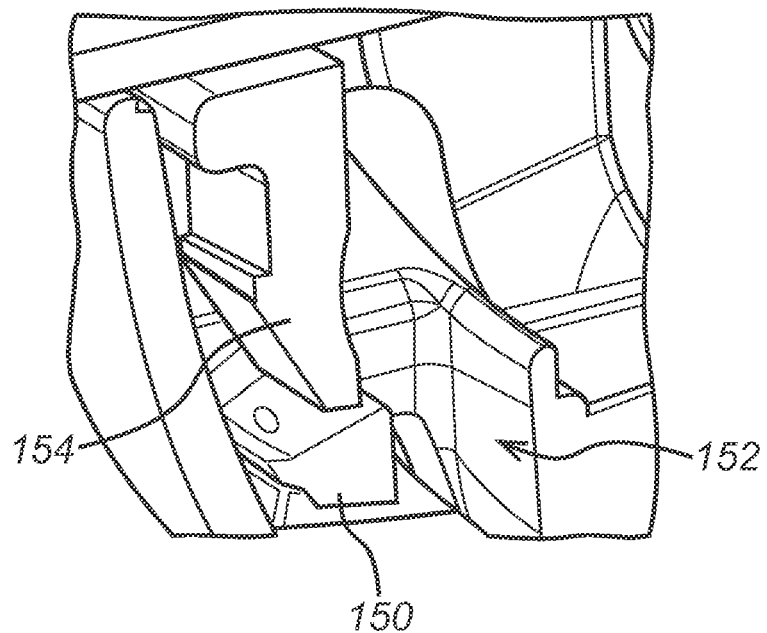
FIG. 7 shows a side view of the trigger and releasable locking mechanism of FIG. 5.

FIG. 7 shows the first portion 150, cut out 152 and protrusion 154 in more detail. As can be seen, the protrusion comprises only flat surfaces, albeit sloped and angled as described above. As can be seen, the distal part of the first portion 150 is angled away from the cut out 152.

Figure 8:
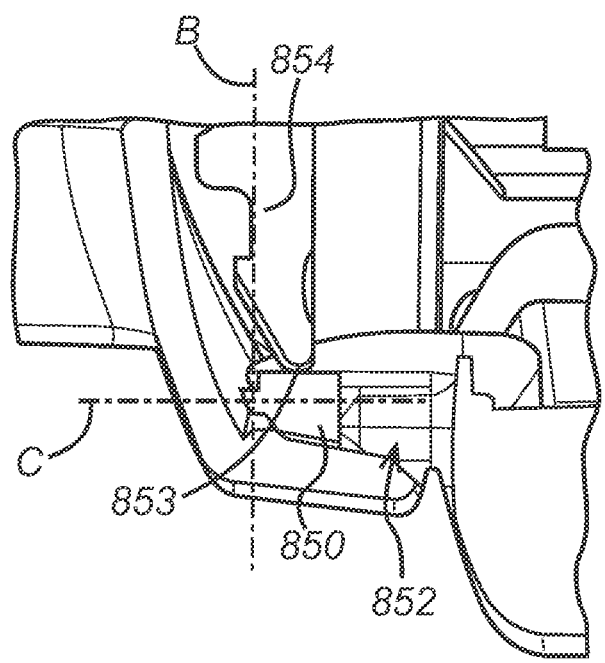
FIG. 8 shows a side view of a trigger and releasable locking mechanism according to the present invention.

FIG. 8 shows a first portion 850, cut out 852 and protrusion 854 of an injection device according to the present invention. In all other respects, the injection device according to the present invention is the same as described above. The protrusion 854 terminates in a curved surface 853, which engages the first portion 850. Because the protrusion is curved where it contacts the actuator, the contact between the protrusion 854 and the actuator is a line (or in some embodiments, a point) rather than a surface.

The curved surface extends substantially over 180° of the end of the protrusion 854 engaging the first portion 850. However, the curved surface could extend substantially over different angles, including 160°, 140°, 120°, 90°, 60° or 40°. Preferably, the curved surface extends over the protrusion enough to ensure that the edge of first portion 850 only ever contacts the protrusion at a curved surface. The curved surface may either be in line or offset or with the centre of the protrusion 854, depending on the preferred implementation.

As shown, the first portion 850 extending from the actuator is substantially planar with respect to the actuator, and with respect to axis A. However, the first portion 850 may be alternatively be angled as shown in FIG. 7, or else could be angled toward the cut-out such that the force required to activate the device if the locking mechanism is not quite in the unlocked portion is reduced.

Axis 'B' is shown in FIG. 8. Axis B is the axis along which protrusion 854 extends from the locking mechanism. Axis B is at an angle of approximately 90° with respect to axis A mentioned above, although other angles of between 45 and 90 degrees, 60 and 90 degrees, 80 and 90 degrees are possible, depending on the preferred implementation.

Axis 'C' is shown in FIG. 8. Axis C is the axis along which first portion 850 extends from the actuator. Axis C is approximately parallel with respect to axis A mentioned above, although other angles of between 0 and 45 degrees, 0 and 20 degrees, 0 and 10 degrees, 0 and 5 degrees are possible, depending on the preferred implementation. Moreover, axis C is at an angle of approximately 90° with respect to axis B mentioned above, although other angles of between 45 and 90 degrees, 60 and 90 degrees, 80 and 90 degrees are possible, depending on the preferred implementation.

It will be appreciated that as the locking mechanism is retracted (by engagement of the sliding sleeve on the body), the curved surface of the protrusion 854 is moved closer to the cut-out 852 in the first portion 850 of the actuator. At some point in this movement, the line (or point, in certain embodiments) of contact between the protrusion and the actuator reaches the edge where the cut-out begins. Here, as the protrusion is moved further in the same direction of retraction, the normal force between the actuator and the locking mechanism moves from being substantially perpendicular to the longitudinal axis, to being at least partly in the direction of retraction because of the arrangement of the curved surface on the protrusion. Thus, when a force is exerted on the actuator when the protrusion is in this position, that force acts to retract the locking mechanism still further, and assist the movement of the locking mechanism into the unlocked position.

In use, such an injection device as described above might be used to deliver substances such as: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity. In addition to these substances, any medicament contained within the injection device may also include other substances, such as inactive ingredients, as a skilled person would appreciate.

It will of course be understood by the person skilled in the art that particular substances are efficacious for use in the treatment or prevention of particular conditions, as is well known in the art. For instance, it is known that antiallergics are efficacious for use in the treatment or prevention of allergies; antihistamines are efficacious for use in the treatment or prevention of hay fever; anti-inflammatories are efficacious for use in the treatment or prevention of inflammation; and so on. Accordingly, any selection of one or more substances listed herein or in the claims for use in the treatment or prevention of one or more conditions for which those substance(s) are known to be efficacious is envisaged.

In a particular example, however, golimumab is known to be efficacious for use in the treatment or prevention of one or more of rheumatoid arthritis, psoriatic arthritis, ankylosing spondylitis or ulcerative colitis, or any combination of rheumatoid arthritis, psoriatic arthritis, ankylosing spondylitis and ulcerative colitis, or all of rheumatoid arthritis, psoriatic arthritis, ankylosing spondylitis and ulcerative colitis.

Golimumab may optionally be used in combination with one or more inactive ingredients such as any or all of L-histidine, L-histidine monohydrochloride monohydrate, sorbitol, polysorbate 80, and water. Golimumab may present in a composition in which golimumab is the only active ingredient. For example, golimumab may administered as SIMPONI®.

It will of course be understood that the present invention has been described above purely by way of example and modifications of detail can be made within the scope of the invention.

The invention claimed is:

1. An injection device comprising:
    an actuator adapted to, when actuated, cause commencement of an injection sequence, wherein the actuator comprises an engagement surface having an edge;

a locking mechanism adapted to be moved between a locked position in which the locking mechanism prevents the actuator from being actuated, and an unlocked position in which the actuator can be actuated to cause commencement of the injection sequence, wherein the locking mechanism comprises a contact portion, wherein the contact portion comprises a protrusion which extends from the locking mechanism and terminates in a curved surface, wherein when the locking mechanism is in the locked position, the curved surface projects against the engagement surface of the actuator, wherein the locking mechanism is adapted such that as the locking mechanism is moved from the locked position to the unlocked position the curved surface moves past the edge of the engagement surface so that the curved surface of the contact portion is not in contact with the engagement surface of the actuator when the locking mechanism is in the unlocked position, wherein the engagement surface is a planar surface on a first portion which extends from the actuator, wherein the locking mechanism slides between the locked position and the unlocked position along a first axis A, wherein the protrusion extends along a second axis B, the first portion extends along a third axis C which is parallel to the first axis A, and wherein the second axis B and third axis C intersect each other with an intersection angle of between 45 and 90 degrees.

2. The injection device of claim 1, wherein the second axis B and third axis C intersect each other with an intersection angle of between 60 and 90 degrees, 80 and 90 degrees, or 90 degrees.

3. The injection device of claim 1, wherein the second axis B intersects both the first axis A and the third axis C.

4. The injection device of claim 1, wherein the actuator moves between a first position in which commencement of the injection sequence is prevented, and a second position in which commencement of the injection sequence occurs.

5. The injection device of claim 1, wherein the locking mechanism is adapted such that the contact portion is in contact with the engagement surface of the actuator when the locking mechanism is in the locked position.

6. The injection device of claim 5, wherein the locking mechanism is adapted such that the curved surface of the contact portion is in contact with the engagement surface over only a sub-part of the contact portion when the locking mechanism is not in the unlocked position.

7. The injection device of claim 1, further comprising a drive mechanism, wherein the actuator comprises a locking surface which inhibits the drive mechanism when the actuator is in the first position and which does not inhibit the drive mechanism when the drive mechanism is in the second position.

8. The injection device of claim 7, further comprising a syringe which is moveable by the drive mechanism on commencement of the injection sequence from a position in which the syringe is wholly contained within a body of the injection device to a position in which a needle of the syringe extends from the body of the injection device via an opening, wherein the drive mechanism is adapted to expel contents of the syringe via the needle when the syringe is in its extended position.

9. The injection device of claim 7, wherein the actuator comprises a pivot, and the actuator is adapted to rotate between the first position and the second position about the pivot.

10. The injection device of claim 9, wherein the axis of the pivot and the second axis B substantially intersect each other with an intersection angle of between 45 and 90 degrees, 60 and 90 degrees, 80 and 90 degrees, or 90 degrees.

11. An injection device according to any one of claims 1, 5, 6, 2, and 3, 4, 7, 9, 10, 8 containing a substance selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

* * * * *